(12) United States Patent
Kim et al.

(10) Patent No.: US 8,513,399 B2
(45) Date of Patent: Aug. 20, 2013

(54) PRIMERS FOR PCR AMPLIFICATION COMPRISING A BASIC PARTS WITHIN THE PRIMER SEQUENCES

(75) Inventors: Hyun Bae Kim, Daejeon (KR); Seong Youl Kim, Daejeon (KR); Jun Mo Gil, Daejeon (KR); Hae Joon Park, Seongnam-si (KR); Han Oh Park, Daejeon (KR)

(73) Assignee: Bioneer Corporation, Daejeon (KR)

( * ) Notice: Subject to any disclaimer, the term of this patent is extended or adjusted under 35 U.S.C. 154(b) by 443 days.

(21) Appl. No.: 12/681,754

(22) PCT Filed: Oct. 2, 2008

(86) PCT No.: PCT/KR2008/005821
§ 371 (c)(1),
(2), (4) Date: Apr. 5, 2010

(87) PCT Pub. No.: WO2009/045067
PCT Pub. Date: Apr. 9, 2009

(65) Prior Publication Data
US 2011/0008845 A1    Jan. 13, 2011

(30) Foreign Application Priority Data
Oct. 5, 2007  (KR) .................... 10-2007-0100507

(51) Int. Cl.
C07H 21/04 (2006.01)
C07H 19/04 (2006.01)
C12Q 1/68 (2006.01)
C12P 19/34 (2006.01)

(52) U.S. Cl.
USPC ..... 536/24.33; 536/23.1; 536/24.3; 536/26.6; 435/6.1; 435/91.1

(58) Field of Classification Search
USPC ............ 536/23.1, 24.3, 24.33, 26.6; 435/6.1, 435/91.1
See application file for complete search history.

(56) References Cited

U.S. PATENT DOCUMENTS
4,683,195 A    7/1987    Mullis et al.
4,683,202 A    7/1987    Mullis
(Continued)

FOREIGN PATENT DOCUMENTS
EP    2050819 A1    4/2009

OTHER PUBLICATIONS

Saiki et al., Enzymatic Amplification of B-Globin Genomic Sequences and restriction Site Analysis for diagnosis of Sickle Cell Anemia, Science, New Series, vol. 230, No. 4732, Dec. 20, 1985, pp. 1350-1354.

(Continued)

*Primary Examiner* — Jezia Riley
(74) *Attorney, Agent, or Firm* — Rothwell, Figg, Ernst & Manbeck, P.C.

(57) ABSTRACT

The present invention relates to primers for PCR amplification comprising abasic parts within the primer sequences and a method for PCR amplification using the same. More precisely, the present invention relates to primers capable of amplifying different templates and having abasic parts complementary to mutated site or polymorphic site of template DNA and a method for PCR amplification comprising the steps of mixing the composition for PCR amplification comprising the primers with nucleic acid template; and performing PCR with the mixture. The primers for PCR amplification of the present invention contain abasic parts not having specific coding information in their nucleotide sequences, so that they can amplify different templates having mutated sites at the same time.

16 Claims, 7 Drawing Sheets

(56) References Cited

U.S. PATENT DOCUMENTS

| | | | |
|---|---|---|---|
| 4,800,159 | A | 1/1989 | Mullis et al. |
| 5,728,528 | A | 3/1998 | Mathies et al. |
| 6,333,178 | B1 | 12/2001 | Livneh et al. |
| 6,361,940 | B1 | 3/2002 | Van Ness et al. |
| 6,410,241 | B1 | 6/2002 | Sykes et al. |
| 7,018,833 | B2 | 3/2006 | Sykes et al. |
| 7,049,098 | B2 | 5/2006 | Sykes et al. |
| 7,060,809 | B2 * | 6/2006 | Wengel et al. ............... 536/23.1 |
| 2007/0099187 | A1 | 5/2007 | Tsukada |

OTHER PUBLICATIONS

Chamberlain et al., Deletion Screening of the Duchnne muscular dystrophy locus via multiplex DNA Amplification Nucleic Acids Research, vol. 16, No. 23, 1988, pp. 11141-11156.

Anonymous, Diagnosis of Duchenne and Becker muscular dystrophies by polymerase chain reaction, A Multicenter study, JAMA, vol. 267, No. 19, May 20, 1992, pp. 2609-2615.

Henegariu, et al., Rapid screening of the Y chromosome in idiopathic sterile men, diagnostic for deletions in AZF, a genetic Y factor expressed during spermatogenesis, Andrologia, vol. 26, 1994, pp. 97-106.

Shuber et al., Efficient 12-mutation testing in the CFTR gene: a general model for complex mutation analysis, Human Molecular Genetics, vol. 2, No. 2, pp. 153-158, 1993.

Mutirangura et al., Multiplex PCR of three dinucleotide repeats in the Prader-Willi/Angelman critical region (15q11-q13): molecular diagnosis and mechanism of uniparental disomy, Human Molecular Genetics, vol. 2, No. 2, pp. 143-151, 1993.

Zimmermann et al., Quantitative multiplex competitive PCR of HIV-1 DNA in a single reaction tube, BioTechniques, vol. 21, Sep. 1996, pp. 480-484.

Zou et al., Identification of new influenza B virus variants by multiplex reverse transcription-PCR and the heteroduplex mobility assay, Journal of Clinical Microbiology, Jun. 1998, pp. 1544-1548.

Supplementary European Search Report from corresponding EP Application No. 08 83 4998, dated Sep. 23, 2010, 2 pages.

U. Candrian et al.: "Use of Inosin-Containing Oligonucleotide Primers for Enzymatic Amplification of Different Alleles of the Gene Coding for Heat-Stable Toxin Type I of Enterotoxigenic *Escherichia coli*," Applied and Environmental Microbiology, vol. 57, No. 4, Apr. 1991, pp. 955-961.

* cited by examiner

PRIMERS FOR PCR AMPLIFICATION COMPRISING A BASIC PARTS WITHIN THE PRIMER SEQUENCES

CROSS REFERENCE TO RELATED APPLICATIONS

This application is a 35 U.S.C. §371 National Phase Entry Application from PCT/KR2008/005821, filed Oct. 2, 2008, and designating the United States, which claims priority under 35 U.S.C. §119 to Korean Patent Application No. 10-2007-0100507 filed Oct. 5, 2007, which is incorporated herein in its entirety.

FIELD OF THE INVENTION

The present invention relates to primers and a method for PCR amplification using the same, more precisely primers capable of amplifying different templates and having abasic parts complementary to mutated site or polymorphic site of the template DNA and a method for PCR amplification using the same.

DESCRIPTION OF THE RELATED ART

The most widely used nucleic acid amplification method, which is known as polymerase chain reaction (referred as "PCR" hereinafter), is composed of repeated cycles comprising denaturation of double stranded DNA, annealing of oligonucleotide primer to DNA template and extension of primer by DNA polymerase (Mullis et al., U.S. Pat. Nos. 4,683,195, 4,683,202 and 4,800,159; Saiki et al, 1985). Oligonucleotide primer used for PCR is designed to be annealed to opposite strand of DNA, and the extended product of primer by DNA polymerase is used as a template for another primer. PCR amplification increases the number of DNA sequence exponentially and the length of the amplified DNA sequence is determined by 5'-end of oligonucleotide primer.

The success of nucleic acid amplification, particularly PCR amplification, depends on target specific annealing of primers. So, it is important to optimize interaction between molecules. It depends on annealing temperature whether a primer anneals into its complete complement only or into a sequence having one or more mismatch in nucleotide sequence. In general, as annealing temperature elevates, chances of annealing of a primer to a specific template which is a complete match to the primer increase, suggesting that chances of the amplification of a target sequence only increase. When annealing temperature is low, tolerance against mismatch between a template and a primer is generated, resulting in the increase of non-targeted sequence amplification. So, by regulating annealing temperature, paring specificity between template and primer can be controlled. For example, if the control group amplified with only one primer produces a different PCR product, it suggests that the single primer anneals into one or more regions of a template. In this case, it is preferred to raise annealing temperature. Considering the effect of raising annealing temperature on annealing specificity of primer, primer annealing may be regulated by temperature, and it is requested to develop an annealing regulating primer system favoring the improvement of annealing specificity of primer, regardless of the primer design.

Not only annealing temperature but also other primer parameters such as primer length, GC content and length of PCR product, have to be considered for annealing specificity of primer. When a primer satisfying the said parameters is used, annealing of primer is specific and annealing specificity for target DNA amplification is improved with overcoming the problems of background and generation of non-specific product by primer. Properly designed primer not only solves the problems of non-specific annealing and background but also facilitates to distinguish cDNA from genome templates in RNA-PCR.

In many cases, primer sequence is not necessarily complementary perfectly to template sequence. The region that is required to be completely matched to a template is 3'-end, because this region is the very region to be extended by DNA polymerase. That is, the said region is most important to secure annealing specificity to a target sequence. 5'-end of the primer is less important for specificity of annealing to target sequence and can be changed in order to deliver a non-complementary additional sequence for example a restriction enzyme site and promoter sequence.

Molecular diagnostic testing or nucleic acid testing is the most rapidly growing field among in-vitro diagnostics, so that it demonstrates approximately 20% annual growth rate in world market. Molecular diagnostic testing took 8% of the total in-vitro diagnostics market in 3 trillion Won scale, in 2003. But in 2008, it takes 13% and demonstrates at least 5 thousand billion Won of sales, indicating annual growth rate of 19%. Molecular diagnostic testing is a sort of PCR, examining virus, bacteria, and fungi causing disease. Precisely, it examines infection with a pathogen by using oligonucleotide (primer, probe) complementary to nucleotide sequence of a specific pathogen gene. According to this method for diagnosing pathogen infection by PCR, target template gene specific primers are used to screen the target gene only, leading to judgment whether it is positive or negative, which is more advantageous than antigen-antibody assay using ELISA (enzyme-linked immuno-sorbent assay) in sensitivity and economic efficiency.

Multiplex PCR is another type of PCR, which facilitates simultaneous amplification of one or more target sequences from a reactant using one or more primer sets. Since this method was first introduced in 1988 (Chamberlain et al., Deletion Screening of the Duchenne muscular dystrophy locus via multiplex DNA Amplification Nucleic Acids Res., 16, 11141-11156, 1988), it has been widely applied in various fields of DNA assay including gene deletion analysis (Anonymous, Diagnosis of Duchenne and Becker muscular dystrophies by polymerase chain reaction, A multicenter study. JAMA 267, 2609-2615, 1992; Henegariu, et al., Rapid screening of the Y chromosome in idiopathic sterile men, diagnostic for deletions in AZF, a genetic Y factor expressed during spermatogenesis, Andrologia, 26, 97-106, 1994), mutation and polymorphism analysis (Shuber et al., Efficient 12-mutation testing in the CFTR gene: a general model for complex mutation analysis, Hum. Mol. Geenet., 2, 153-158, 1993; Mutirangura et al., Multiplex PCR of three dinucleotide repeats in the Prader-Willi/Angelman critical region (15q11-q13): molecular diagnosis and mechanism of uniparental disomy, *Hum. Mol. Genet.*, 2, 143-151, 1993), quantitative analysis (Zimmermann et al., Quantitative multiplex competitive PCR of HIV-1 DNA in a single reaction tube, *BioTechniques* 21, 480-484, 1996), and RNA detection (Zou et al., Identification of new influenza B virus variants by multiplex reverse transcription-PCR and the heteroduplex mobility assay, *J. Clin. Microbiol.*, 36, 1544-1548, 1998). Particularly, in diagnosing infectious disease, this method is valuable and important to identify virus, bacteria, fungi and/or parasites.

However, multiplex PCR frequently produces complicated results because of artificial facts involved in amplification, making errors. Therefore, the result therefrom includes 'false-negative' caused by reaction failure and 'false-positive' resulted from amplification of a fake product. The false-positive result is generated because primer is annealed to a totally different sequence even if it is related to the original recognized sequence. In multiplex PCR, hybridization kinetics of primer has to be designed to be similar to the hybridization kinetics of another primer different but used for the same multiplex reactant. Annealing temperature and primer concentration can be calculated to some degree, but other general conditions for multiplex reaction are determined by experience. As primer sets increase in number, chances of non-specific priming increase. So, whenever each primer set is added, conditions have to be changed. Moreover, artificial factors generated by competition with reactant (for example, exhaustion of primers) increase in multiplex PCR and difference of yields between unequally amplified products become bigger as cycles repeat. Therefore, optimization of reaction conditions for multiplex PCR takes a lot of time and labors. Each multiplex PCR need diversal unique reaction condition, so that development of a novel diagnostic method requires high costs.

Single nucleotide polymorphism (referred as "SNP" hereinafter) means that one different nucleotide pair in nucleotide polymorphism causes individual differences according to race, age or gender in nucleotide sequence of chromosome, which is largely found in DNA nucleotide sequence polymorphism. In general, one per 1,000 nucleotides becomes mutated in human gene. Even among patients having the same disease, individual difference is observed, which seems to be because of difference in SNP. SNP analysis methods developed so far are exemplified by SSCP (Single Strand Conformation Polymorphism), PCR-RELP (Restriction Fragment Length Polymorphism), Allele-specific PCR (AS-PCR), Tm-shift genotyping using GC-tail primer, DASH (Dynamic allele-specific hybridization), Fluorescence polarization, Taqman (5'-exonuclease assay), Molecular Beacons, OLA (Oligonucleotide ligase assay), Pyrosequencing, single nucleotide extension, and MALDI-TOF (Matrix Assisted Laser Desorption/Ionization-Time of Flight), etc. These methods are for analysis of SNP using template specific oligonucleotide or fluorescence labeled probe oligonucleotide.

When a target gene exists in the form of multiple polymorphic gene containing mutated loci in the sequence of the gene, primers are needed to be designed according to the types of polymorphism to have complementary sequence to the corresponding mutated loci. To do so, all the gene specific polymorphic sequences have to be identified. If a polymorphic gene is not identified, detection of all target genes might not be accomplished. Therefore, in the case that a specific nucleotide sequence contains limited mutation or polymorphism, a method that is able to amplify the mutated loci simply by using a pair of primers is required.

SUMMARY OF THE INVENTION

The present invention is designed to overcome the problems of the conventional PCR method. Therefore, it is an object of the present invention to provide primers for PCR amplification in which different polymorphic sites of a target gene are substituted with abasic parts and a method for PCR facilitating common amplification of nucleic acids of different templates having mutated or polymorphic loci in its nucleotide sequence.

DETAILED DESCRIPTION OF THE PREFERRED EMBODIMENTS

To achieve the above object, the present invention provides primers for PCR amplification comprising abasic parts within the primer sequences.

In this invention, "abasic part" indicates nucleoside that does not comprise specific coding information. Since it does not have coding information, nucleotide of corresponding template DNA can be any of adenine, guanine, cytosine and thymine. The abasic part herein is preferably located in a region corresponding to mutated site and/or polymorphic site of primer sequence. The primers of the present invention are the primers for PCR amplification comprising abasic parts selected from the group consisting of dSpacer (5'-O-dimethoxytrityl-1',2'-dideoxyribose-3'-[(2-cyanoethyl)-(N,N-diisopropyl)]-phosphoramidite), 1'-OMe-dSpacer (5'-O-dimethoxytrityl-1'-methoxy-2'-dideoxyribose-3'-[(2-cyanoethyl)-(N,N-diisopropyl)]-phosphoramidite), PC Spacer Phosphoamidite ([4-(4,4'-Dimethoxytrityloxy)butyramidomethyl)-1-(2-nitrophenyl)-ethyl]-2-cyanoethyl-(N,N-diisopropyl)-phosphoramidite), rSpacer CE Phosphoamidite (5'-O-Dimethoxytrityl-1'-Deoxyribose-2'-O-Triisopropylsilyloxymethyl-3'-[(2-cyanoethyl)-(N,N-diisopropyl)]-phosphoramidite), Spacer C12 CE Phosphoamidite (12-(4,4'-Dimethoxytrityloxy)-dodecyl-1-[(2-cyanoethyl)-(N,N-diisopropyl)]-phosphoramidite), Spacer Phosphoamidite 18 (18-O-Dimethoxytritylhexaethyleneglycol,1-[(2-cyanoethyl)-(N,N-diisopropyl)]-phosphoramidite), Spacer Phosphoamidite 9 (9-O-Dimethoxytrityl-triethyleneglycol,1-[(2-cyanoethyl)-(N,N-diisopropyl)]-phosphoramidite), and Spacer Phosphoamidite C3 (3-(4,4'-Dimethoxytrityloxy)propyl-1-[(2-cyanoethyl)-(N,N-diisopropyl)]-phosphoramidite), but not always limited thereto. Even if a primer is synthesized from another phosphoramidite having slight changes in structure, this primer can be included in the criteria of the present invention as long as it comprises same abasic parts in the primer sequence.

Insertion of abasic parts in the primer sequence facilitates the amplification of template having different polymorphic sites in one gene with one primer set. The number of abasic parts in primer is not limited, but 1-10 abasic parts in 3'-end, internal sequence and 5'-end are preferred and 1-3 abasic parts in them are more preferred. If the number of abasic parts is more than 10, Tm of primer becomes lower significantly, resulting in unsuccessful annealing to template DNA sequence, indicating unsuccessful PCR reaction. If so, the object of the present invention to equally amplify different templates having mutated sites cannot be accomplished.

The present invention also provides a composition for PCR amplification comprising reaction buffer, 4 different dNTPs, DNA polymerase, probe and the said primers for PCR amplification.

The conventional PCR reaction buffer comprising Tris-HCl, KCl, $(NH_4)_2SO_4$, $MgSO_4$, $MgCl_2$, etc, can be properly modified for the preparation of the reaction buffer for this invention. The said 4 different dNTPs are dATP, dTTP, dGTP and dCTP. DNA polymerase is not limited to a specific enzyme. In a preferred embodiment of the present invention, PCR was performed using Taq DNA polymerase, K/en Taq DNA polymerase or Pfu DNA polymerase. Concentrations of the primers for PCR amplification in the invention are 1-50 pmole in 20 uL PCR reaction mixture. The primer concentration can be determined by those skilled in the art.

The composition for PCR amplification of the present invention can additionally include dye and/or stabilizer for convenience of experiment, prevention of contamination by PCR reaction products, stabilization of DNA polymerase and dNTP, and improvement of reactivity. the dye is selected from the group consisting of Bromophenol blue, Xylene cyanole, Bromocresol red and Cresol red, but not always limited thereto. And the stabilizer can be selected from the group consisting of gelatin, bovine serum albumin, Thesit, PEG-8000 and polyol, but not always limited thereto. The content of dye in the composition is 0.0001-0.01 weight %, preferably 0.001-0.005 weight % and more preferably 0.001-0.003 weight %. The content of stabilizer in the composition is 2-1,000 mM, preferably 100-500 mM and more preferably 100-300 mM.

The present invention provides a method for PCR amplification using the PCR primers comprising abasic parts within the primer sequences.

The said method comprises the step of mixing template DNA with the composition for PCR amplification containing the primers comprising abasic parts within the primer sequences; and the step of performing PCR amplification with the mixture.

The method for PCR amplification of the present invention is used for the common amplification of different nucleic acid templates having mutated sites and/or polymorphic sites in their nucleotide sequences, but not always limited thereto. Both of the primers used for PCR amplification herein can contain abasic parts of the present invention. Or one of the primers can contain abasic parts and the other can be a normal primer without abasic parts.

PCR is performed by repeating the cycle of denaturation, annealing and extension, and this PCR amplification mechanism is well understood by those skilled in the art. Denaturation, annealing and extension are preferably performed respectively at 85-95° C. for 1-60 seconds, at 40-70° C. for 1-60 seconds and at 50-75° C. for 1-60 seconds. Temperature range and reaction time can be properly regulated. In a preferred embodiment of the present invention, when a primer had one abasic substitution in its sequence, melting temperature (referred as "Tm" hereinafter) was approximately 8° C. lower and when a primer had one abasic substitution particularly at 3'-end, Tm was approximately 1.5° C. lower. To compensate the lowered Tm by abasic parts, nucleotides complementary to the template are added to both ends of the primer, so that PCR reactivity can be regulated. When complementary nucleotides are added to 3'-end, Tm increases approximately 0.5° C. every time 2 nucleotides are added. When a primer has one, two or three abasic part substitutions and at the same time 5 complementary nucleotides are added to 5'-end, Tm is lower respectively about 4° C., 10° C. and 18° C. Tm can vary from kind of DNA polymerase, length of primer, nucleotide of primer and reaction conditions. When a primer is designed to have mutated sites in its sequence, conditions for temperature equivalence can be settled on the Tm regulation. Specificity of PCR can be controlled by introducing abasic parts and extending the length of primer. So, different templates having mutated sites in their sequences can be commonly amplified by using only one pair of primers.

In preferred embodiments of the present invention (Example 1 and Example 2), PCR was performed using human genomic DNA as a template with primers having abasic substitution using different DNA polymerases. As a result, when Taq DNA polymerase was used and one nucleotide was substituted, Tm decreased by approximately 3-6° C. When Pfu DNA polymerase was used and one nucleotide was substituted, Tm decreased by approximately 6° C. When Klen Taq DNA polymerase was used and one nucleotide was substituted, Tm was approximately 1-2° C. lowered, which did not affect PCR reaction, though. Therefore, it was confirmed that a primer comprising abasic parts can be used with different types of DNA polymerases. Proper and optimum abasic primer conditions can be determined according to each DNA polymerase. So, considering the determined conditions, construction conditions for a primer having mutated sites that can secure temperature equivalence can be established.

In a preferred embodiment of the present invention (Example 4), when one nucleotide was substituted with abasic part at 3'-end of a primer, Tm was approximately 1.5° C. lowered, compared with the control primer set. When one nucleotide was substituted in internal sequence, Tm decreased by approximately 8° C. In the meantime, when one nucleotide was substituted in internal sequence and 5 nucleotides complementary to template were added to 3'-end, Tm decreased by approximately 4° C., compared with the control primer set. When 2 nucleotides were substituted in internal sequence and 5 nucleotides complementary to template were added to 3'-end, Tm was approximately 10° C. lowered. When 3 nucleotides were substituted and 5 nucleotides complementary to template were added to 3'-end, Tm decreased by approximately 18° C. When one nucleotide was substituted in internal sequence and 1 nucleotide complementary to template was added to 3'-end, Tm was approximately 5° C. lowered. When one nucleotide was substituted in internal sequence and 3 nucleotides complementary to template were added to 3'-end, Tm was approximately 4.5° C. lowered. When one nucleotide was substituted in internal sequence and 5 nucleotides complementary to template were added to 3'-end, Tm was approximately 4° C. lowered. The results are shown in Table 1.

TABLE 1

| Sample number of Example 4 | Primer modification | | | ΔTm (value compared with control group) |
|---|---|---|---|---|
| | Number of nucleotide substituted with abasic part | | Number of nucleotide added 3'-end | |
| | Internal sequence | 3'-end | | |
| Sample 2 | — | 1 | — | −1.5° C. |
| Sample 3 | 1 | — | — | −8° C. |
| Sample 4 | 2 | — | 5 | −10° C. |
| Sample 5 | 3 | — | 5 | −18° C. |
| Sample 6 | 1 | — | 1 | −5° C. |
| Sample 7 | 1 | — | 3 | −4.5° C. |
| Sample 8 | 1 | — | 5 | −4° C. |

The above results are summarized herein again. When 1 nucleotide was substituted in internal sequence, Tm decreased by approximately 6.5° C., compared with when 1 nucleotide was substituted in each end. When 1 nucleotide, 2 nucleotides, and 3 nucleotides were substituted in internal sequence and 5 complementary nucleotides were added to each 3'-end, Tm decreased by approximately 6° C.-8° C. each time when the number of nucleotide was increased. When 1 nucleotide was substituted in internal sequence and 2 complementary nucleotides were added to 3'-end each time (for example, 1 complementary nucleotide, 3 complementary nucleotides and 5 complementary nucleotides were added), Tm increased by approximately 0.5° C. each time two complementary nucleotides were added.

Based on the above results, conditions for primer construction that can realize temperature equivalence in each primer during primer design can be established. Insertion of abasic parts in primer can minimize margin of Tm during the construction of nucleotide sequence. Therefore, specificity of PCR reaction can be improved.

Advantageous Effect

As explained hereinbefore, the primers for PCR amplification of the present invention comprising abasic parts within the primer sequences are capable of amplifying different templates having mutated sites in the nucleotide sequence at the same time by using one pair of primers by introducing abasic parts in the primer sequences.

BRIEF DESCRIPTION OF THE DRAWINGS

The application of the preferred embodiments of the present invention is best understood with reference to the accompanying drawings, wherein:

In FIG. 7-FIG. 9, reddish purple line in each graph indicates the decrease of fluorescence level (Y axis) according to the increase of temperature (X axis).

FIG. 10 discloses SEQ ID NOS 34-52, respectively, in order of appearance.

FIG. 11 and FIG. 12 are graphs showing the results of real-time PCRs performed with the primer in which 1 nucleotide is substituted with dSpacer in internal sequence (dS), with the primer in which 1 nucleotide is substituted with 1'-OMe-dSpacer (Me-dS), or the primer comprising normal nucleotides (Reg) and probe. Each line indicates fluorescence level according to the increase of the number of PCR cycle of three standard samples having different concentrations.

EXAMPLES

Figure 1:
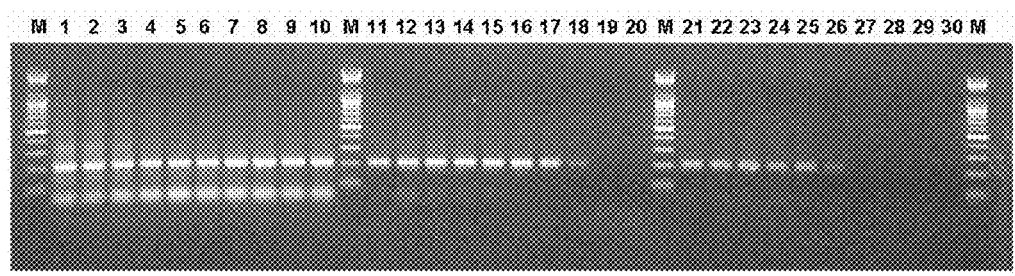
FIG. 1 is an electrophoresis photograph showing the result of polymerase chain reaction (referred as "PCR" hereinafter) amplification with p55/p53 primer set containing abasic parts using Taq DNA polymerase.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Examination of Efficacy of PCR Amplification Using p55/p53 Primers Comprising Abasic Parts The reactivity and specificity of nucleic acid amplification using abasic primers constructed from p55/p53 primer set were investigated by performing PCR with Taq DNA polymerase (Bioneer, referred as "Taq" hereinafter) and Klen Taq DNA polymerase (Bioneer, referred as "Klen Taq" hereinafter). Human genomic DNA was used as template DNA and the following three pairs of primers were used: The control primer set was composed of p55 primer (nucleotide sequence: 5'-CTC TTC CTG CAG TAC TCC CCT GC-3', SEQ. ID. NO: 1) and p53 primer (nucleotide sequence: 5'-GCC CCA GCT CAC CAT CGC TA-3', SEQ. ID. NO: 2) (amplification size: 211 bp, 15 pmole/20 µl reaction); The first sample group primer set was composed of No2-1F (SEQ. ID. NO: 3) prepared from p55 primer by substituting the $10^{th}$ nucleotide from 5'-end "C" with "N" (dSpacer, Glen Research, Cat. No. 10-1914-xx) and No2-1R (SEQ. ID. NO: 4) prepared from p53 primer by substituting the $9^{th}$ nucleotide from 5'-end "T" with "N" (dSpacer) (15 pmole/20 µl reaction); The second sample group primer set was composed of No2-2F (SEQ. ID. NO: 5) prepared from p55 primer by substituting the $10^{th}$ and $11^{th}$ nucleotides from 5'-end "CA" with "NN" (dSpacer) and No2-2R (SEQ. ID. NO: 6) prepared from p53 primer by substituting the $9^{th}$ and $10^{th}$ nucleotides from 5'-end "TC" with "NN" (dSpacer) (15 pmole/20 µl reaction).

As an enzyme for PCR, Taq DNA polymerase (1 U/20 µl reaction) or Klen Taq DNA polymerase (Bioneer, referred as "Klen Taq" hereinafter) (0.4 U/20 µl reaction) was used. In addition, dNTP mixture (2.5 mM of each dATP, dCTP, dGTP and dTTP) was added as an additive for the reaction (2 µl/20 µl reaction). As 10× reaction buffer for Taq or Klen Taq polymerase, 100 mM Tris-HCl, 400 mM KCl, and 15 mM $MgCl_2$ were added (pH 9.0, 2 µl/20 µl reaction).

PCR was performed as follows. When Taq was used, amplification was performed as follows; predenaturation at 94° C. for 5 minutes, denaturation at 94° C. for 30 seconds, annealing at 45° C.-59° C. for 50 seconds, extension at 72° C. for 50 seconds, 38 cycles from denaturation to extension, and final extension at 72° C. for 5 minutes. When Klen Taq was used, amplification was performed as follows; non-specific reaction at 37° C. for 5 minutes, predenaturation at 94° C. for 5 minutes, denaturation at 94° C. for 30 seconds, annealing at 45° C.-59° C. for 50 seconds, extension at 72° C. for 50 seconds, 38 cycles from denaturation to extension, and final extension at 72° C. for 5 minutes. Results of PCR were confirmed by electrophoresis using 0.5× TBE buffer (Trizma nucleotide, Boric Acid and 0.5M EDTA, pH 8.0) containing 2.0% agarose.

FIG. 1 illustrates the results of agarose gel electrophoresis with the products of PCR performed with the control primer set, the first sample group primer set and the second sample group primer set respectively using Taq. Lane 1-Lane 10, Lane 11-Lane 20 and Lane 21-Lane 30 respectively present the results obtained from using different primers, which are the control primers, the first sample group primer set and the second sample group primer set. At that time, temperatures for annealing were 45.1° C., 45.3° C., 46.3° C., 47.7° C., 49.4° C., 51.4° C., 53.3° C., 55.3° C., 57.6° C. and 59.0° C., respectively. M herein indicates 100~2,000 bp DNA size marker (Bioneer). This DNA size marker contains 13 double-stranded DNA fragments; 100 bp, 200 bp, 300 bp, 400 bp, 500 bp, 600 bp, 700 bp, 800 bp, 900 bp, 1,000 bp, 1,200 bp, 1,600 by and 2,000 by size fragments. In the case of the control, two strong bands were observed. The upper band is the target band and the lower band indicates the primer dimer band. The band presenting non-specific product is the one shown in the upper of the target band with leaving dragging track.

As shown in FIG. 1, when the first sample group primer set and the second sample group primer set were used, non-specific reaction and dimer pattern were reduced. In particular, the first sample group primer set was more effective in reducing non-specific reaction and dimer pattern than the second sample group primer set. In addition, high PCR product was confirmed.

Each Tm was compared. In the control group (lane 1-lane 10), template was all amplified at annealing temperatures of 45.1° C., 45.3° C., 46.3° C., 47.7° C., 49.4° C., 51.4° C., 53.3° C., 55.3° C., 57.6° C. and 59.0° C. In the meantime, when the first sample group primer set was used (lane 11-lane 20), template was only amplified at annealing temperature of 55.3° C. (lane 18). Thus, $\Delta Tm=59.0°$ C.–55.3° C.=3.7° C. When the second sample group primer set was used (lane 21-lane 30), template was only amplified at annealing temperature of 51.4° C. (lane 26). Thus, $\Delta Tm=59.0°$ C.–51.4° C.=7.6° C.

Figure 2:
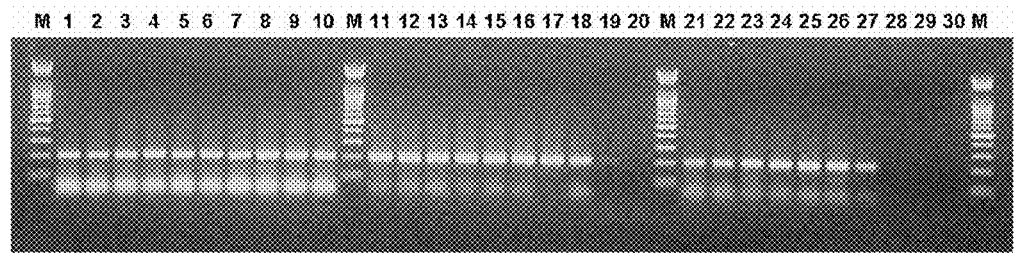
FIG. 2 is an electrophoresis photograph showing the result of PCR amplification with p55/p53 primer set containing abasic parts using Klen Taq DNA polymerase.

FIG. 2 is an electrophoresis photograph showing the results of agarose gel electrophoresis with the products of PCR performed by using the control primer set, the first sample group primer set and the second sample group primer set in the presence of Klen Taq. Descriptions on lane 1-lane 30 and M are the same as given in Example 1. As shown in FIG. 2, when the first sample group primer set and the second sample group primer set were used, non-specific reaction and dimer pattern were reduced.

Each Tm was compared by the same manner as described in FIG. 1. $\Delta Tm$ of the first sample group primer set was 1.4° C. and $\Delta Tm$ of the second sample group primer set was 5.7° C.

The above results indicate that the first sample group primers in which 1 nucleotide is substituted in internal sequence reduce non-specific reaction in the presence of Taq and Klen Taq, and the second sample group primers in which 2 nucleotides are substituted in internal sequence reduce non-specific reaction in the presence of Taq and Klen Taq as well. That is, the introduction of abasic parts does not increase non-specific reaction but reduce non-specific reaction. Therefore, the primers of the present invention comprising abasic parts which are not complementary to template were confirmed to retain reaction specificity as primers. When a specific nucleotide of the sample group primer was substituted with abasic part (dSpacer), annealing temperature for PCR was rather lowered regardless of DNA polymerase types.

Example 2

Examination of Efficacy of PCR Amplification Using p63/p55 Primers Comprising Abasic Parts The reactivity and specificity of nucleic acid amplification using abasic primers constructed from p63/p55 primer set were investigated by performing PCR with Taq DNA polymerase and Pfu DNA polymerase (Bioneer, referred as "Pfu" hereinafter). Human genomic DNA was used as template DNA and the following three pairs of primers were used: The control primer set was composed of p55 primer (nucleotide sequence: 5'-CTC TTC CTG CAG TAC TCC CCT GC-3', SEQ. ID. NO: 1) and p63 primer (nucleotide sequence: 5'-GGC CAC TGA CAA CCA CCC TTA CC-3', SEQ. ID. NO: 7) (amplification size: 447 bp, 15 pmole/20 µl reaction); The first sample group primer set was composed of No2-1F and No3-1R (SEQ. ID. NO: 8) prepared from p63 primer by substituting the $10^{th}$ nucleotide from 5'-end "C" with "N" (dSpacer) (15 pmole/20 µl reaction); The second sample group primer set was composed of No2-2F and No3-2R (SEQ. ID. NO: 9) prepared from p63 primer by substituting the $10^{th}$ and $11^{th}$ nucleotides from 5'-end "CA" with "NN" (dSpacer) (15 pmole/20 µl reaction).

As an enzyme for PCR, Taq or Pfu polymerase (1 U/20 µl reaction) was used. In addition, dNTP mixture (2.5 mM of each dATP, dCTP, dGTP and dTTP) was added as an additive for the reaction (2 µl/20 µl reaction). As 10× reaction buffer for Taq polymerase, 100 mM Tris-HCl, 400 mM KCl, and 15 mM $MgCl_2$ were added (pH 9.0, 2 µl/20 µl reaction). As 10× reaction buffer for Pfu polymerase, 200 mM Tris-HCl, 100 mM KCl, 100 mM $(NH_4)_2SO_4$, 20 mM $MgSO_4$, 1% Triton X-100, and 1 mg/ml of acetylated BSA were added (pH 8.8, 2 µl/20 µl reaction).

PCR was performed as follows; non-specific reaction at 37° C. for 5 minutes, predenaturation at 94° C. for 5 minutes, denaturation at 94° C. for 30 seconds, annealing at 45° C.-59° C. for 50 seconds, extension at 72° C. for 50 seconds, 38 cycles from denaturation to extension, and final extension at 72° C. for 5 minutes. Results of PCR were confirmed by electrophoresis using 0.5× TBE buffer containing 2.0% agarose.

Figure 3:
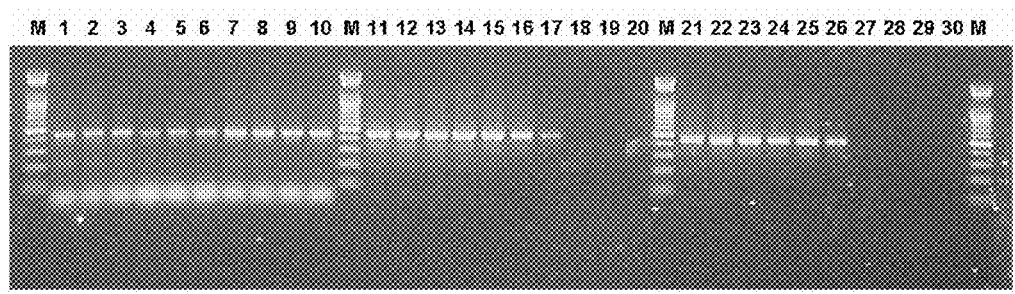
FIG. 3 is an electrophoresis photograph showing the result of PCR amplification with p63/p55 primer set containing abasic parts using Taq DNA polymerase.

FIG. 3 is an electrophoresis photograph showing the results of agarose gel electrophoresis with the products of PCR performed by using the control primer set, the first sample group primer set and the second sample group primer set in the presence of Taq. Descriptions on lane 1-lane 30 and M are the same as given in Example 1. As shown in FIG. 3, when the first sample group primer set and the second sample group primer set were used, non-specific reaction and dimer pattern were reduced. In particular, the first sample group primer set was more effective in reducing non-specific reaction and dimer pattern than the second sample group primer set. $\Delta Tm$ was 5.7° C. and 7.6° C. respectively.

Figure 4:
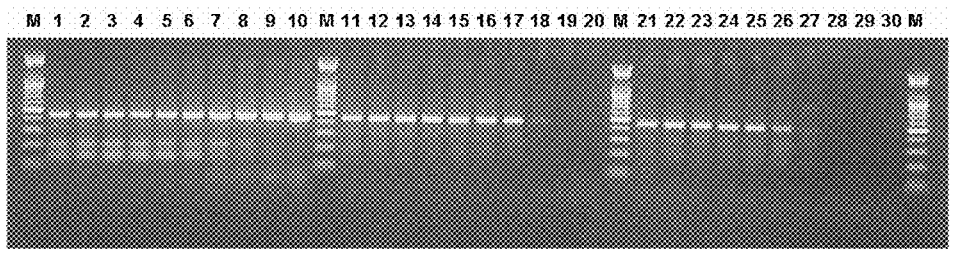
FIG. 4 is an electrophoresis photograph showing the result of PCR amplification with p63/p55 primer set containing abasic parts using Pfu DNA polymerase.

FIG. 4 is an electrophoresis photograph showing the results of agarose gel electrophoresis with the products of PCR performed by using the control primer set, the first sample group primer set and the second sample group primer set in the presence of Pfu. Descriptions on lane 1-lane 30 and M are the same as given in Example 1. As shown in FIG. 3, when the first sample group primer set and the second sample group primer set were used, non-specific reaction and dimer pattern were reduced. In particular, the second sample group primer set was more effective in reducing non-specific reaction and dimer pattern than the first sample group primer set. ΔTm was 5.7° C. and 7.6° C. respectively.

The above results indicate that the first sample group primers and the second sample group primers increase PCR reactivity and reduce non-specific reaction in the presence of Taq and Klen Taq. Therefore, abasic primers were confirmed to have efficacy for PCR reactivity and specificity. When a specific nucleotide of the sample group primer was substituted with abasic part (dSpacer), annealing temperature for PCR was rather lowered regardless of DNA polymerase types.

Example 3

Efficacy of DNA Polymerase on Abasic Primer Construction Conditions

Abasic primers were constructed with the control primer sets by substituting 1 nucleotide (sample 2) at 3'-end, substituting 1 nucleotide (sample 3) in internal sequence, substituting 2 nucleotides in internal sequence and adding 5 complementary nucleotides to 3'-end (sample 4), substituting 3 nucleotides in internal sequence and adding 5 complementary nucleotides to 3'-end (sample 5), substituting 1 nucleotide in internal sequence and adding 1 complementary nucleotide to 3'-end (sample 6), substituting 1 nucleotide in internal sequence and adding 3 complementary nucleotides to 3'-end (sample 7) and substituting 1 nucleotide in internal sequence and adding 5 complementary nucleotides to 3'-end (sample 8).

Human genomic DNA was used as template DNA. Each primer set was used at the concentration of 12-40 pmole/20 μl reaction. Sample 1 was the control primer set comprising F_AP_CONT primer (nucleotide sequence: 5'-CGT GTT TGT GCC TGT CCT GG-3', SEQ. ID. NO: 10) and R_AP_CONT primer (nucleotide sequence: 5'-CCG CTT CTT GTC CTG CTT GC-3', SEQ. ID. NO: 11) (amplification size: 127 bp). Sample 2 was the primer set prepared from the control primer set by substituting 1 nucleotide at 3'-end, which comprised F_AP_CONT_3-1N primer (nucleotide sequence: 5'-CGT GTT TGT GCC TGT CCT GN-3', SEQ. ID. NO: 12) and R_AP_CONT_3-1N primer (nucleotide sequence: 5'-CCG CTT CTT GTC CTG CTT GN-3', SEQ. ID. NO: 13). Sample 3 was the primer set prepared from the control primer set by substituting 1 nucleotide in internal sequence, which comprised F_AP_CONT_I-1N primer (nucleotide sequence: 5'-CGT GTT TGT GCN TGT CCT GG-3', SEQ. ID. NO: 14) and R_AP_CONT_I-1N primer (nucleotide sequence: 5'-CCG CTT CTT GTN CTG CTT GC-3', SEQ. ID. NO: 15). Sample 4 was the primer set prepared from the control primer set by substituting 2 nucleotides in internal sequence and adding 5 complementary nucleotides to 3'-end, which comprised F_AP_CONT_I-2N_3+5M primer (nucleotide sequence: 5'-CGT GTT TNT GCN TGT CCT GGG AGA G-3', SEQ. ID. NO: 16) and R_AP_CONT_I-2N_3+5M primer (nucleotide sequence: 5'-CCG CTT NTT GTN CTG CTT GCT TAC C-3', SEQ. ID. NO: 17). Sample 5 was the primer set prepared from the control primer set by substituting 3 nucleotides in internal sequence and adding 5 complementary nucleotides to 3'-end, which comprised F_AP_CONT_I-3N_3+5M primer (nucleotide sequence: 5'-CGT GTT TNT GCN TGT NCT GGG AGA G-3', SEQ. ID. NO: 18) and R_AP_CONT_I-3N_3+5M primer (nucleotide sequence: 5'-CCG CTT NTT GTN CTG NTT GCT TAC C-3', SEQ. ID. NO: 19). Sample 6 was the primer set prepared from the control primer set by substituting 1 nucleotide in internal sequence and adding 1 complementary nucleotide to 3'-end, which comprised F_AP_CONT_I-1N_3+1M primer (nucleotide sequence: 5'-CGT GTT TGT GCN TGT CCT GGG-3', SEQ. ID. NO: 20) and R_AP_CONT_1N_3+1M primer (nucleotide sequence: 5'-CCG CTT CTT GTN CTG CTT GCT-3', SEQ. ID. NO: 21). Sample 7 was the primer set prepared from the control primer set by substituting 1 nucleotide in internal sequence and adding 3 complementary nucleotides to 3'-end, which comprised F_AP_CONT_I-1N_3+3M primer (nucleotide sequence: 5'-CGT GTT TGT GCN TGT CCT GGG AG-3', SEQ. ID. NO: 22) and R_AP_CONT_I-1N_3+3M primer (nucleotide sequence: 5'-CCG CTT CTT GTN CTG CTT GCT TA-3', SEQ. ID. NO: 23). Sample 8 was the primer set prepared from the control primer set by substituting 1 nucleotide in internal sequence and adding 5 complementary nucleotides to 3'-end, which comprised F_AP_CONT_I-1N_3+5M primer (nucleotide sequence: 5'-CGT GTT TGT GCN TGT CCT GGG AGA G-3', SEQ. ID. NO: 24) and R_AP_CONT_I-1N_3+5M primer (nucleotide sequence: 5'-CCG CTT CTT GTN CTG CTT GCT TAC C-3', SEQ. ID. NO: 25).

As an enzyme for PCR, Klen Taq polymerase (0.4 U/20 μl reaction) was used. In addition, dNTP mixture (2.5 mM of each dATP, dCTP, dGTP and dTTP) was added as an additive for the reaction (2 μl/20 μl reaction). As 10× reaction buffer for Klen Taq polymerase, 100 mM Tris-HCl, 400 mM KCl, and 15 mM MgCl$_2$ were added (pH 9.0, 2 μl/20 μl reaction).

PCR was performed as follows; predenaturation at 94° C. for 5 minutes, denaturation at 94° C. for 30 seconds, annealing at 55° C.-70° C. or 46° C.-61° C. for 50 seconds, extension at 72° C. for 50 seconds, 40 cycles from denaturation to extension, and final extension at 72° C. for 5 minutes. Results of PCR were confirmed by electrophoresis using 0.5× TBE buffer containing 2.0% agarose.

Figure 5:
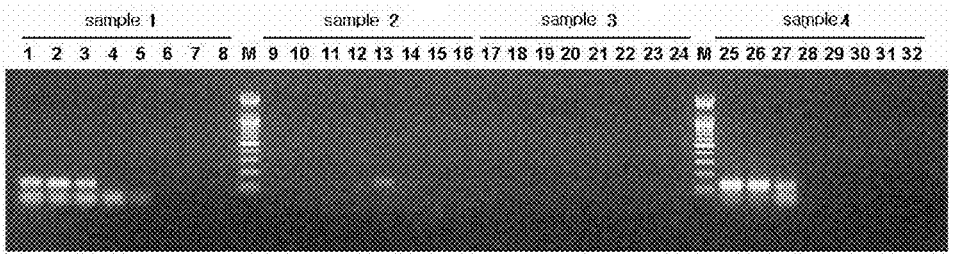
FIG. 5 is an electrophoresis photograph showing the results of PCRs using Klen Taq DNA polymerase respectively with the control primer set, with the primer set in which 1 nucleotide was substituted with abasic part in 3'-end, with the primer set in which 1 nucleotide was substituted with abasic part in internal sequence, and with the primer set in which 2 nucleotides were substituted with abasic parts in internal sequence and 5 complementary nucleotides were added to 3'-end.
Figure 6:
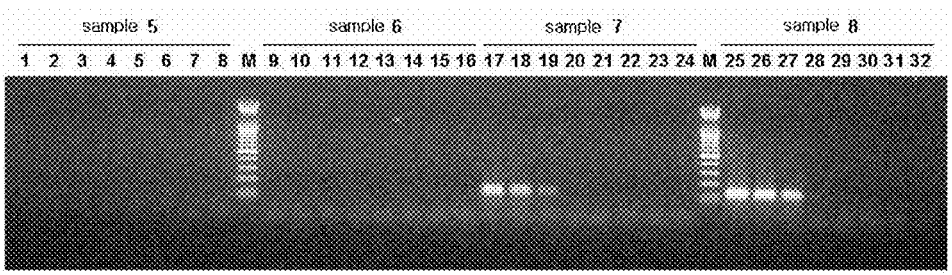
FIG. 6 is an electrophoresis photograph showing the results of PCRs using Klen Taq DNA polymerase respectively with the control primer set, with the primer set in which 3 nucleotides were substituted with abasic parts in internal sequence and 5 complementary nucleotides were added to 3'-end, with the primer set in which 1 nucleotide was substituted with abasic part in internal sequence and 1 complementary nucleotide was added to 3'-end, with the primer set in which 1 nucleotide was substituted with abasic part in internal sequence and 3 complementary nucleotides were added to 3'-end, and with the primer set in which 1 nucleotide was substituted with abasic part in internal sequence and 5 complementary nucleotides were added to 3'-end.
Figure 7:
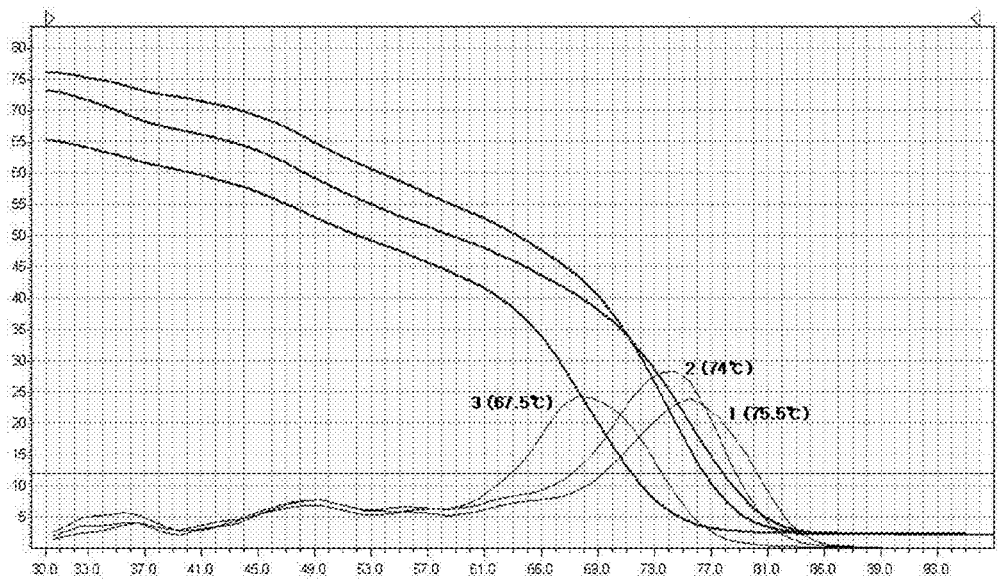
FIG. 7 is a graph illustrating the melting curve of a pair of primers having different locations of abasic parts, analyzed by real-time gene amplification apparatus.
Figure 8:
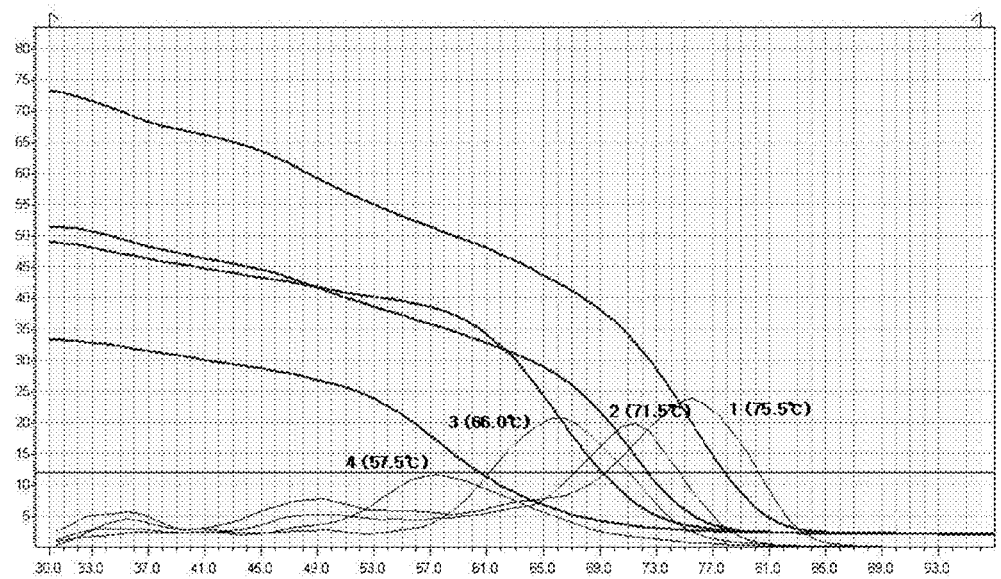
FIG. 8 is a graph illustrating the melting curve of a pair of primers having different number of abasic parts in internal sequences, analyzed by real-time gene amplification apparatus.
Figure 9:
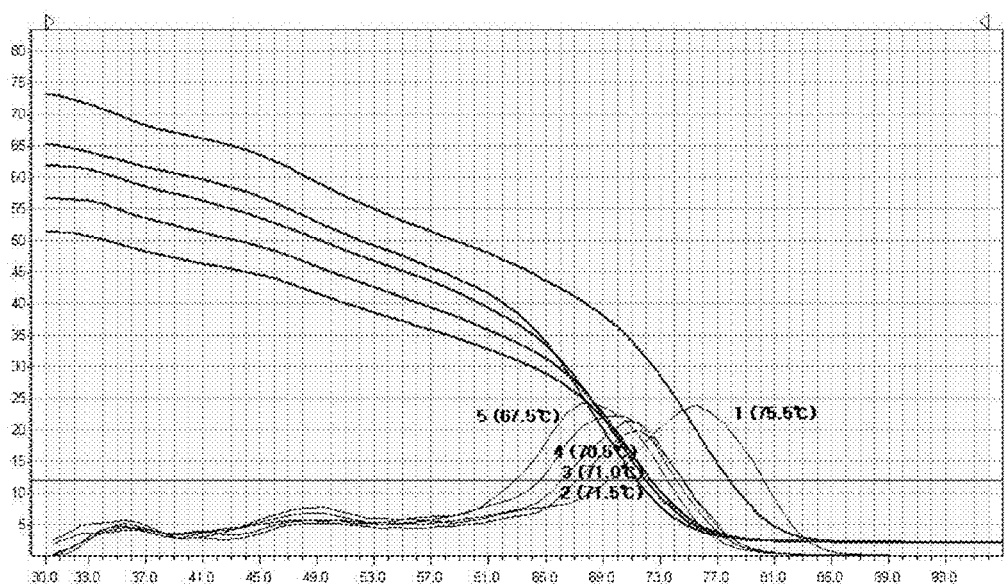
FIG. 9 is a graph illustrating the melting curve of a pair of primers having 1 nucleotide substituted with abasic part in internal sequence and having different number of nucleotides added to 3'-end.
Figure 10:
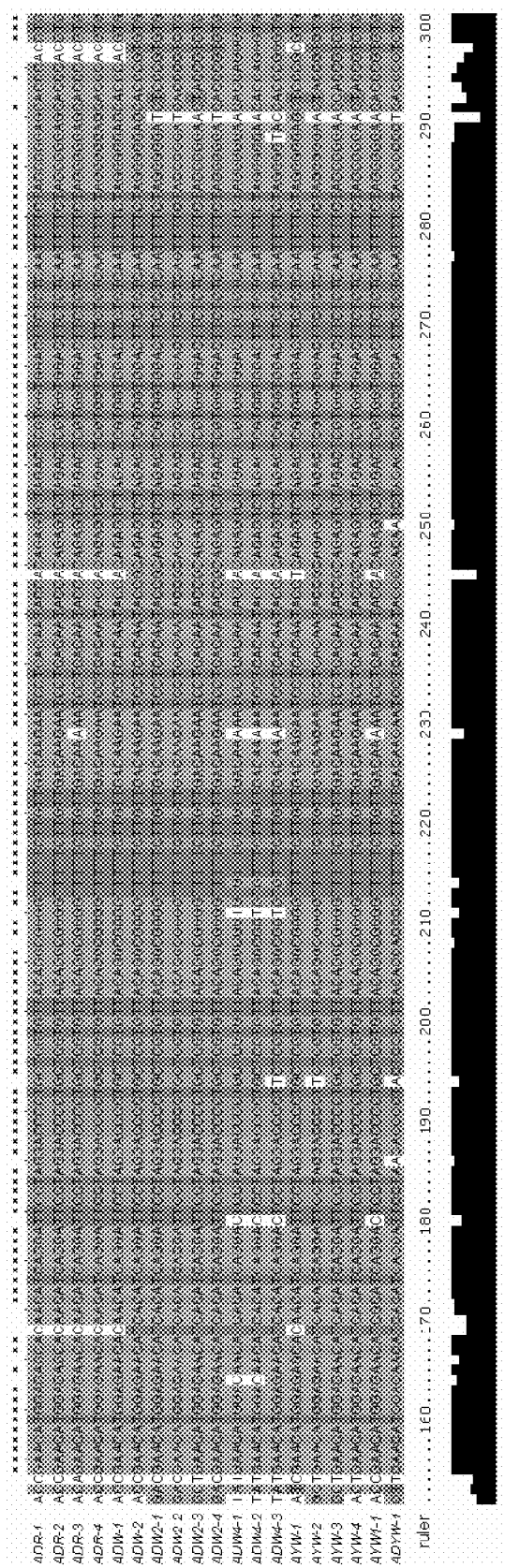
FIG. 10 is a diagram showing the substitution of 1 nucleotide with abasic part in internal sequence of a primer corresponding to polymorphic site of S gene of hepatitis B virus.
Figure 1T:
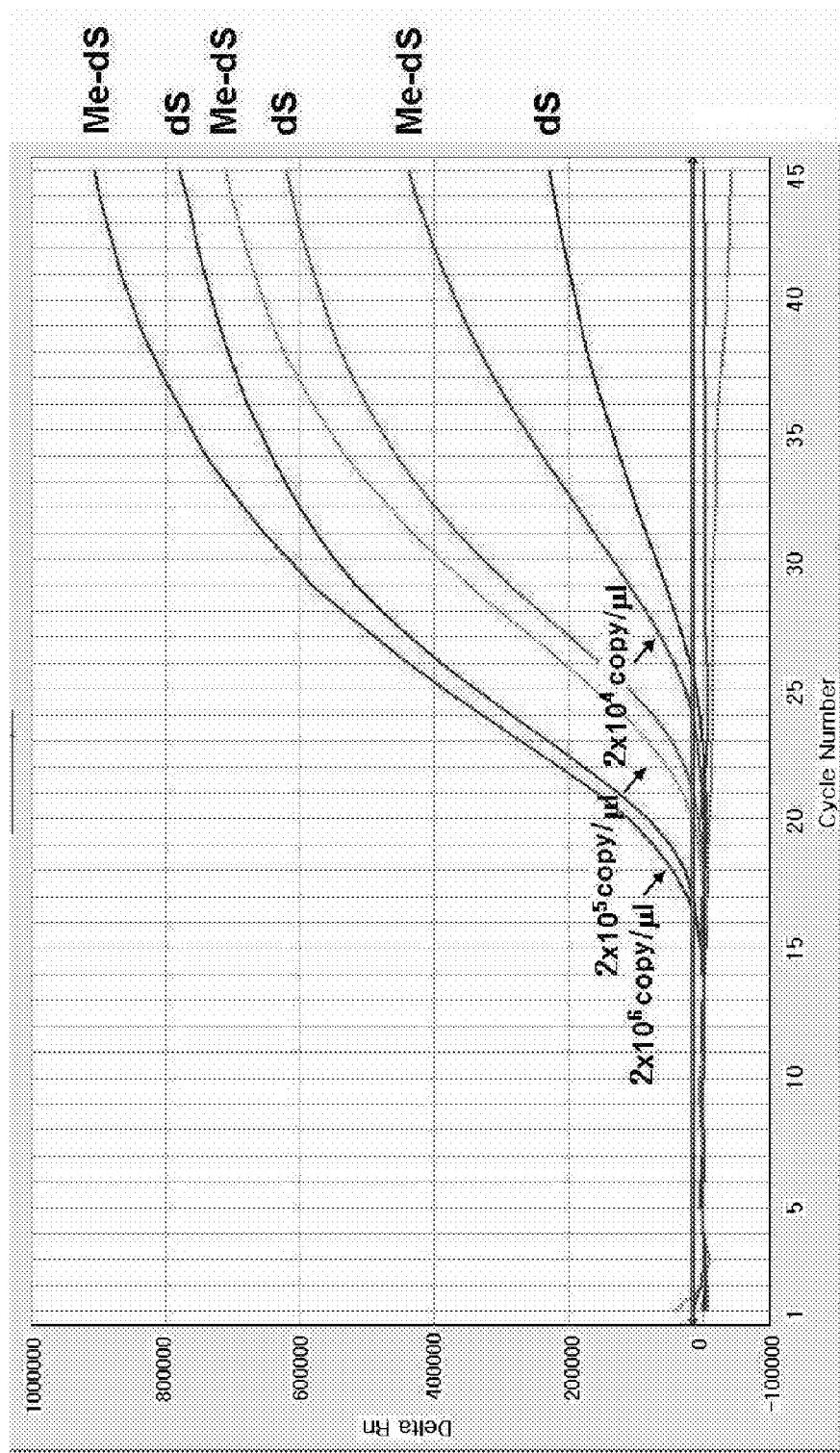

FIG. 5 and FIG. 6 illustrate the results of agarose gel electrophoresis with the products of PCR performed with the 8 different primer sets in the presence of Klen Taq. Description on M is the same as given in Example 1.

In FIG. 5, lane 1-lane 8 present the results obtained by using the sample 1 primer set at different annealing temperatures of 59.4° C., 61.4° C., 63.3° C., 65.3° C., 67.6° C., 69° C., 69.7° C. and 70.2° C. Lane 9-lane 16 present the results obtained by using the sample 2 primer set at different annealing temperatures of 55.5° C., 56.3° C., 57.1° C., 59.4° C., 61.4° C., 63.3° C., 65.3° C. and 67.6° C. Lane 17-lane 24 present the results obtained by using the sample 3 primer set at different annealing temperatures of 46.1° C., 46.5° C., 47.3° C., 48.7° C., 50.4° C., 52.4° C., 54.3° C. and 56.3° C. Lane 25-lane 32 present the results obtained by using the sample 4 primer set at different annealing temperatures of 48.7° C., 50.4° C., 52.4° C., 54.3° C., 56.3° C., 58.6° C., 60° C. and 60.7° C. M indicates 100 by DNA size marker.

In FIG. 6, lane 1-lane 8 present the results obtained by using the sample 5 primer set at different annealing temperatures of 46.1° C., 46.5° C., 47.3° C., 48.7° C., 50.4° C., 52.4° C., 54.3° C. and 56.3° C. Lane 9-lane 16 present the results obtained by using the sample 6 primer set at different annealing temperatures of 46.1° C., 46.5° C., 47.3° C., 48.7° C., 50.4° C., 52.4° C., 54.3° C. and 56.3° C. Lane 17-lane 24 present the results obtained by using the sample 7 primer set at different annealing temperatures of 46.1° C., 46.5° C., 47.3° C., 48.7° C., 50.4° C., 52.4° C., 54.3° C. and 56.3° C. Lane 25-lane 32 present the results obtained by using the sample 8 primer set at different annealing temperatures of 48.7° C., 50.4° C., 52.4° C., 54.3° C., 56.3° C., 58.6° C., 60° C. and 60.7° C.

As shown in FIG. 5 and FIG. 6, the sample 1 primer set amplified PCR product at annealing temperatures up to 63.3°

C. The sample 2 primer set amplified PCR product at the annealing temperature range of 61.4° C.~63.3° C. No PCR products were confirmed with the sample 3 primer set, the sample 5 primer set and the sample 6 primer set. The sample 4 primer set amplified PCR product at annealing temperatures up to 52.4° C. The sample 7 primer set amplified PCR product at annealing temperatures of up to 47.3° C. The sample 8 primer set amplified PCR product at annealing temperatures of up to 52.4° C.

Figure 12:
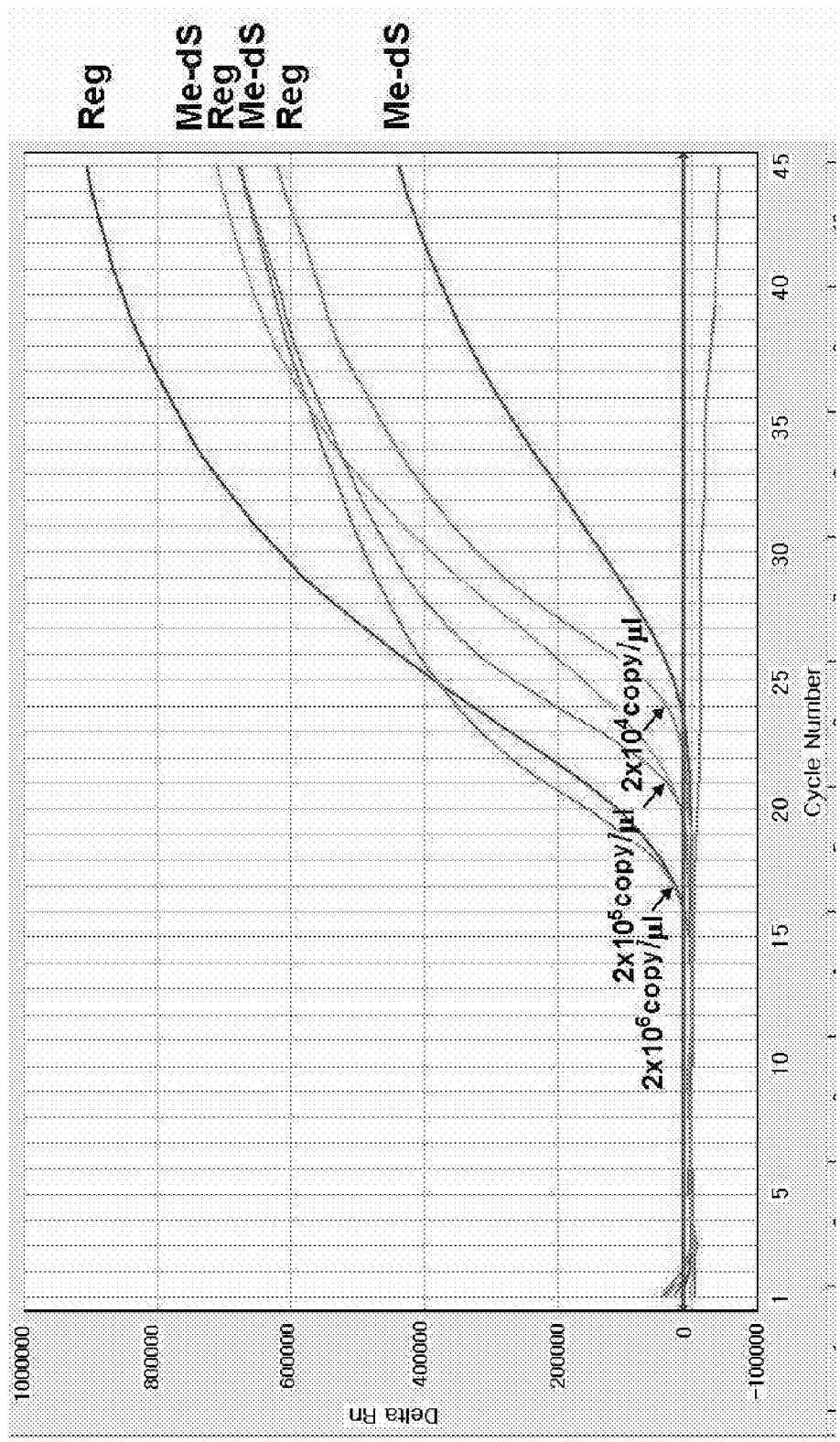

The above results indicate that the primers prepared from the control primer set by substituting 1 nucleotide (sample 2) at 3'-end and substituting 2 nucleotides in internal sequence and adding 5 complementary nucleotides to 3'-end (sample 4) can induce PCR amplification and at this time reaction temperature is approximately 11° C. and 10° C. lowered, compared with the control primer set. The primers prepared from the control primer set by substituting 1 nucleotide in internal sequence and adding 3 complementary nucleotides to 3'-end (sample 7) and substituting 1 nucleotide in internal sequence and adding 5 complementary nucleotides to 3'-end (sample 8) can induce PCR amplification and at this time reaction temperature is approximately 16° C. and 11° C. lowered, compared with the control primer set.

Example 4

Melting Curve Examination by Dissociation for Apurine Primer Construction Conditions Each Tm of 8 apurine primer sets confirmed in Example 3 was measured by melting curve. 0.3 nmole/20 μl reaction of complementary reverse primer (nucleotide sequence: 5'-G GTA AGC AAG CAG GAC AAG AAG CGG-3', SEQ. ID. NO: 26) was added respectively to 0.3 nmol of the forward primer (nucleotide sequence: 5'-CGT GTT TGT GCC TGT CCT GG-3', SEQ. ID. NO: 10) of sample 1 of Example 3, 0.5 nmol of the forward primer (nucleotide sequence:5'-CGT GTT TGT GCC TGT CCT GN-3', SEQ. ID. NO: 12) of sample 2, 1.0 nmol of the forward primer (nucleotide sequence: 5'-CGT GTT TGT GCN TGT CCT GG-3', SEQ. ID. NO: 14) of sample 3, 0.5 nmol of the forward primer (nucleotide sequence: 5'-CGT GTT TNT GCN TGT CCT GGG AGA G-3', SEQ. ID. NO: 16) of sample 4, 1.0 nmole of the forward primer (nucleotide sequence: 5'-CGT GTT TNT GCN TGT NCT GGG AGA G-3', SEQ. ID. NO: 18) of sample 5, 1.0 nmol of the forward primer (nucleotide sequence: 5'-CGT GTT TGT GCN TGT CCT GGG-3', SEQ. ID. NO: 20) of sample 6, 1.0 nmol of the forward primer (nucleotide sequence: 5'-CGT GTT TGT GCN TGT CCT GGG AG-3', SEQ. ID. NO: 22) of sample 7 and 0.5 nmol of the forward primer (nucleotide sequence: 5'-CGT GTT TGT GCN TGT CCT GGG AGA G-3', SEQ. ID. NO: 24) of sample 8. As additives for the reaction, 10× reaction buffer (100 mM Tris-HCl, 400 mM KCl, 50 mM $MgCl_2$, pH 9.0) (2 μl/20 μl reaction) and 2 μl of 10× SYBR Green were added. SYBR Green is fluorescent dye intercalating in minor groove of double-stranded DNA strand. If temperature is low, double strand is strongly formed and at this time the fluorescent dye is intercalated a lot, resulting in high fluorescence. On the contrary, if temperature is high, double strand is unfastened into single strand, and thus the fluorescent dye is not easily intercalated in between, resulting in the difficulty in measuring fluorescence. Melting curve was made by real-time gene amplification apparatus (Exicycler™, Bioneer corporation). Reaction conditions at this time were as follows. Predenaturation was induced at 94° C. for 5 minutes, which stood at 20° C. for 5 minutes. Then, the mixture stood for 10 seconds each temperature when temperature was raised from 30° C. to 97° C. degree by degree.

FIG. 7 is a graph showing the melting curves according to the locations of apurine part substitution in the control primer set (sample 1). Line 1 indicates the melting curve for the sample 1 primer set (control), line 2 indicates the melting curve for the sample 2 primer set, and line 3 indicates the melting curve for the sample 3 primer set. FIG. 8 is a graph showing the melting curves according to the number of nucleotides substituted in internal sequence. Line 1 indicates the melting curve for the sample 1 primer set (control), line 2 indicates the melting curve for the sample 8 primer set, line 3 indicates the melting curve for the sample 4 primer set, and line 4 indicates the melting curve for the sample 5 primer set. FIG. 9 is a graph showing the melting curves according to the number of complementary nucleotide added to 3'-end and the substitution of 1 nucleotide in internal sequence of the control primer set. Line 1 indicates the melting curve for the sample 1 primer set (control), line 2 indicates the melting curve for the sample 8 primer set, line 3 indicates the melting curve for the sample 7 primer set, line 4 indicates the melting curve for the sample 6 primer set, and line 5 indicates the melting curve for the sample 3 primer set.

According to the above results, when 1 nucleotide was substituted with abasic part at 3'-end of the control primer set, Tm was approximately 1.5° C. lowered. When 1 nucleotide was substituted with abasic part in internal sequence, Tm was approximately 8° C. lowered (see FIG. 7). And, when 5 complementary nucleotides were added to 3'-end and 1, 2 or 3 nucleotides were substituted with abasic parts in internal sequence, Tm was respectively 4° C., 10° C. and 18° C. lowered, compared with that of the control primer set (see FIG. 8). When 1 nucleotide was substituted with abasic part in internal sequence and nucleotides were added to 3'-end, Tm increased by 0.5° C. every time 2 nucleotides were added (see FIG. 9).

Example 5

Efficacy of PCR Using Abasic Primers Prepared by Substituting 1 Nucleotide in Internal Sequence Exhibiting Polymorphism of Hepatitis B Virus (HBV) S Gene Efficacy of PCR using abasic primers prepared by substituting 1 nucleotide in internal sequence exhibiting polymorphism of hepatitis B virus S gene and probes corresponding thereto was investigated. It was also investigated whether different kinds of dSpacer produced different results or not. To do so, abasic primers having same sequence were constructed by using dSpacer and 1'-OMe-dSpacer (see FIG. 10). Nucleotide sequences of the constructed primers and probes are as shown in Table 2. 5'-end of the probe was labeled with FAM fluorescent dye and 3'-end of the probe was labeled with TAMRA fluorescent dye.

TABLE 2

| Primer containing 1 nucleotide substitution in internal sequence | Forward primer | Reverse primer | Probe |
|---|---|---|---|
| dSpacer primer | SEQ. ID. NO: 27 | SEQ. ID. NO: 30 | SEQ. ID. NO: 33 |
| 1'-OMe-dSpacer primer | SEQ. ID. NO: 28 | SEQ. ID. NO: 31 | SEQ. ID. NO: 33 |
| Normal primer | SEQ. ID. NO: 29 | SEQ. ID. NO: 32 | SEQ. ID. NO: 33 |

Real-time PCR was performed with the abasic primers and probes using Applied Biosystems 7500 FAST real-time PCR system (Applied Biosystems, USA). Particularly, 1 µl of the forward primer (10 pmol), 1 µl of the reverse primer (10 pmol), 1 µl of probe (5 pmol) and 1 U of Taq were mixed to make 20 µl of reaction mixture. In addition, 1 µl of dNTP mixture (2.5 mM of each dATP, dCTP, dGTP and dTTP) was also added thereto (1 µl/20 µl reaction). As 10× reaction buffer for Taq polymerase, 200 mM Tris-HCl, 350 mM KCl, and 15 mM MgCl$_2$ (pH 9.0) were added (2 µl /20 µl reaction). PCR was performed as follows; ① at 95° C. for 12 minutes, ② at 95° C. for 20 seconds, ③ at 57° C. for 40 seconds, ④ 40 cycles of ②~③. And the results are shown in FIG. 11 and FIG. 12.

As shown in FIG. 11, the primer in which 1 nucleotide was substituted with dSpacer in internal sequence and the primer in which 1 nucleotide was substituted with 1'-OMe-dSpacer exhibited equal Ct value. As shown in FIG. 12, the primer in which 1 nucleotide was substituted with 1'-OMe-dSpacer in internal sequence and the normal primer without substitution demonstrated equal Ct value. The above results indicate that the abasic primers of the present invention can be effectively used for the detection of hepatitis B virus.

SEQUENCE LISTING

Sequence listing is attached herewith.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

```
                        SEQUENCE LISTING

<160> NUMBER OF SEQ ID NOS: 52

<210> SEQ ID NO 1
    <211> LENGTH: 23
    <212> TYPE: DNA
    <213> ORGANISM: Artificial Sequence
    <220> FEATURE:
    <223> OTHER INFORMATION: synthetic primer

<400> SEQUENCE: 1
ctcttcctgc agtactcccc tgc                                              23

<210> SEQ ID NO 2
    <211> LENGTH: 20
    <212> TYPE: DNA
    <213> ORGANISM: Artificial Sequence
    <220> FEATURE:
    <223> OTHER INFORMATION: synthetic primer

<400> SEQUENCE: 2
gccccagctc accatcgcta                                                  20

<210> SEQ ID NO 3
    <211> LENGTH: 22
    <212> TYPE: DNA
    <213> ORGANISM: Artificial Sequence
    <220> FEATURE:
    <223> OTHER INFORMATION: synthetic primer
    <220> FEATURE:
    <221> NAME/KEY: misc_feature
    <222> LOCATION: (9)..(9)
    <223> OTHER INFORMATION: abasic part: dSpacer nucleoside

<400> SEQUENCE: 3
ctcttcctga gtactccct gc                                                22

<210> SEQ ID NO 4
    <211> LENGTH: 19
    <212> TYPE: DNA
    <213> ORGANISM: Artificial Sequence
    <220> FEATURE:
    <223> OTHER INFORMATION: synthetic primer
    <220> FEATURE:
    <221> NAME/KEY: misc_feature
    <222> LOCATION: (8)..(8)
    <223> OTHER INFORMATION: abasic part: dSpacer nucleoside

<400> SEQUENCE: 4
```
gccccagcca ccatcgcta                                              19

<210> SEQ ID NO 5
<211> LENGTH: 21
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (9)..(10)
<223> OTHER INFORMATION: abasic part: dSpacer nucleoside

<400> SEQUENCE: 5
ctcttcctgg tactcccctg c                                           21

<210> SEQ ID NO 6
<211> LENGTH: 18
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (8)..(9)
<223> OTHER INFORMATION: abasic part: dSpacer nucleoside

<400> SEQUENCE: 6
gccccagcac catcgcta                                               18

<210> SEQ ID NO 7
<211> LENGTH: 23
<212> TYPE: DNA
<213> ORGANISM: Artificial Sequence
<220> FEATURE:
<223> OTHER INFORMATION: synthetic primer

<400> SEQUENCE: 7
ggccactgac aaccaccctt acc                                         23

<210> SEQ ID NO 8
<211> LENGTH: 22
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (9)..(9)
<223> OTHER INFORMATION: abasic part: dSpacer nucleoside

<400> SEQUENCE: 8
ggccactgaa accaccctta cc                                          22

<210> SEQ ID NO 9
<211> LENGTH: 21
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (9)..(10)
<223> OTHER INFORMATION: abasic part: dSpacer nucleoside

<400> SEQUENCE: 9
ggccactgaa ccacccttac c                                           21

-continued

```
<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
cgtgtttgtg cctgtcctgg                                                    20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
ccgcttcttg tcctgcttgc                                                    20

<210> SEQ ID NO 12
<211> LENGTH: 19
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (19)..(19)
<223> OTHER INFORMATION: abasic part: dSpacer nucleoside

<400> SEQUENCE: 12
cgtgtttgtg cctgtcctg                                                     19

<210> SEQ ID NO 13
<211> LENGTH: 19
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (19)..(19)
<223> OTHER INFORMATION: abasic part: dSpacer nucleoside

<400> SEQUENCE: 13
ccgcttcttg tcctgcttg                                                     19

<210> SEQ ID NO 14
<211> LENGTH: 19
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (11)..(11)
<223> OTHER INFORMATION: abasic part: dSpacer nucleoside

<400> SEQUENCE: 14
cgtgtttgtg ctgtcctgg                                                     19

<210> SEQ ID NO 15
<211> LENGTH: 19
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
```

```
<222> LOCATION: (11)..(11)
<223> OTHER INFORMATION: abasic part: dSpacer nucleoside

<400> SEQUENCE: 15
ccgcttcttg tctgcttgc                                                    19

<210> SEQ ID NO 16
<211> LENGTH: 23
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (7)..(7)
<223> OTHER INFORMATION: abasic part: dSpacer nucleoside
<220> FEATURE:
<221> NAME/KEY: misc_feature
<222> LOCATION: (10)..(10)
<223> OTHER INFORMATION: abasic part: dSpacer nucleoside

<400> SEQUENCE: 16
cgtgttttgc tgtcctggga gag                                               23

<210> SEQ ID NO 17
<211> LENGTH: 23
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (6)..(6)
<223> OTHER INFORMATION: abasic part: dSpacer nucleoside
<220> FEATURE:
<221> NAME/KEY: misc_feature
<222> LOCATION: (10)..(10)
<223> OTHER INFORMATION: abasic part: dSpacer nucleoside

<400> SEQUENCE: 17
ccgcttttgt ctgcttgctt acc                                               23

<210> SEQ ID NO 18
<211> LENGTH: 22
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (7)..(7)
<223> OTHER INFORMATION: abasic part: dSpacer nucleoside
<220> FEATURE:
<221> NAME/KEY: misc_feature
<222> LOCATION: (10)..(10)
<223> OTHER INFORMATION: abasic part: dSpacer nucleoside
<220> FEATURE:
<221> NAME/KEY: misc_feature
<222> LOCATION: (13)..(13)
<223> OTHER INFORMATION: abasic part: dSpacer nucleoside

<400> SEQUENCE: 18
cgtgttttgc tgtctgggag ag                                                22

<210> SEQ ID NO 19
<211> LENGTH: 22
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
```

```
<222> LOCATION: (6)..(6)
<223> OTHER INFORMATION: abasic part: dSpacer nucleoside
<220> FEATURE:
<221> NAME/KEY: misc_feature
<222> LOCATION: (10)..(10)
<223> OTHER INFORMATION: abasic part: dSpacer nucleoside
<220> FEATURE:
<221> NAME/KEY: misc_feature
<222> LOCATION: (13)..(13)
<223> OTHER INFORMATION: abasic part: dSpacer nucleoside

<400> SEQUENCE: 19
ccgcttttgt ctgttgctta cc                                            22

<210> SEQ ID NO 20
<211> LENGTH: 20
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (11)..(11)
<223> OTHER INFORMATION: abasic part: dSpacer nucleoside

<400> SEQUENCE: 20
cgtgtttgtg ctgtcctggg                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (11)..(11)
<223> OTHER INFORMATION: abasic part: dSpacer nucleoside

<400> SEQUENCE: 21
ccgcttcttg tctgcttgct                                               20

<210> SEQ ID NO 22
<211> LENGTH: 22
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (11)..(11)
<223> OTHER INFORMATION: abasic part: dSpacer nucleoside

<400> SEQUENCE: 22
cgtgtttgtg ctgtcctggg ag                                            22

<210> SEQ ID NO 23
<211> LENGTH: 22
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (11)..(11)
<223> OTHER INFORMATION: abasic part: dSpacer nucleoside

<400> SEQUENCE: 23
ccgcttcttg tctgcttgct ta                                            22
```

```
<210> SEQ ID NO 24
<211> LENGTH: 24
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (11)..(11)
<223> OTHER INFORMATION: abasic part: dSpacer nucleoside

<400> SEQUENCE: 24
cgtgtttgtg ctgtcctggg agag                                              24

<210> SEQ ID NO 25
<211> LENGTH: 24
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (11)..(11)
<223> OTHER INFORMATION: abasic part: dSpacer nucleoside

<400> SEQUENCE: 25
ccgcttcttg tctgcttgct tacc                                              24

<210> SEQ ID NO 26
<211> LENGTH: 25
<212> TYPE: DNA
<213> ORGANISM: Artificial Sequence
<220> FEATURE:
<223> OTHER INFORMATION: synthetic primer

<400> SEQUENCE: 26
ggtaagcaag caggacaaga agcgg                                             25

<210> SEQ ID NO 27
<211> LENGTH: 22
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (10)..(10)
<223> OTHER INFORMATION: abasic part: dSpacer nucleoside

<400> SEQUENCE: 27
tcgtgttaca gcggggtttt tc                                                22

<210> SEQ ID NO 28
<211> LENGTH: 22
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (10)..(10)
<223> OTHER INFORMATION: abasic part: 1'-OMe-dSpacer nucleoside

<400> SEQUENCE: 28
tcgtgttaca gcggggtttt tc                                                22

<210> SEQ ID NO 29
<211> LENGTH: 23
<212> TYPE: DNA
<213> ORGANISM: Artificial Sequence
```

```
<220> FEATURE:
<223> OTHER INFORMATION: synthetic primer

<400> SEQUENCE: 29
tcgtgttaca ggcggggttt ttc                                            23

<210> SEQ ID NO 30
<211> LENGTH: 27
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (7)..(7)
<223> OTHER INFORMATION: abasic part: dSpacer nucleoside

<400> SEQUENCE: 30
tagaaaatga gagaagtcca ccacgag                                        27

<210> SEQ ID NO 31
<211> LENGTH: 27
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (7)..(7)
<223> OTHER INFORMATION: abasic part: 1'-OMe-dSpacer nucleoside

<400> SEQUENCE: 31
tagaaaatga gagaagtcca ccacgag                                        27

<210> SEQ ID NO 32
<211> LENGTH: 28
<212> TYPE: DNA
<213> ORGANISM: Artificial Sequence
<220> FEATURE:
<223> OTHER INFORMATION: synthetic primer

<400> SEQUENCE: 32
tagaaaattg agagaagtcc accacgag                                       28

<210> SEQ ID NO 33
<211> LENGTH: 28
<212> TYPE: DNA
<213> ORGANISM: Artificial Sequence
<220> FEATURE:
<223> OTHER INFORMATION: synthetic primer

<400> SEQUENCE: 33
tgttgacaag aatcctcaca ataccgca                                       28

<210> SEQ ID NO 34
<211> LENGTH: 150
<212> TYPE: DNA
<213> ORGANISM: Hepatitis B virus

<400> SEQUENCE: 34
accgaacatg gagagcacaa catcaggatt cctaggaccc ctgctcgtgt tacaggcggg    60
gtttttcttg ttgacaagaa tcctcacaat accacagagt ctagactcgt ggtggacttc   120
tctcaatttt ctaggggag cacccacgtg                                     150

<210> SEQ ID NO 35
<211> LENGTH: 150
```

```
<212> TYPE: DNA
<213> ORGANISM: Hepatitis B virus

<400> SEQUENCE: 35
accgaacatg gagagcacaa catcaggatt cctaggaccc ctgctcgtgt tacaggcggg      60 gttttttcttg ttgacaagaa tcctcacaat accacagagt ctagactcgt ggtggacttc    120
tctcaatttt ctaggggag cacccacgtg                                       150

<210> SEQ ID NO 36
<211> LENGTH: 150
<212> TYPE: DNA
<213> ORGANISM: Hepatitis B virus

<400> SEQUENCE: 36
acagaacatg gagaacacaa catcaggatt cctaggaccc ctgctcgtgt tacaggcggg      60 gttttttcttg ttgacaaaaa tcctcacaat accacagagt ctagactcgt ggtggacttc    120
tctcaatttt ctaggggag cacccacgtg                                       150

<210> SEQ ID NO 37
<211> LENGTH: 150
<212> TYPE: DNA
<213> ORGANISM: Hepatitis B virus

<400> SEQUENCE: 37
accgaacatg gagaacacaa catcaggatt cctaggaccc ctgctcgtgt tacaggcggg      60 gttttttcttg ttgacaagaa tcctcacaat accacagagt ctagactcgt ggtggacttc    120
tctcaatttt ctaggggag cacccacgtg                                       150

<210> SEQ ID NO 38
<211> LENGTH: 150
<212> TYPE: DNA
<213> ORGANISM: Hepatitis B virus

<400> SEQUENCE: 38
accgaacatg gagaacacaa catcaggatt cctaggaccc ctgctcgtgt tacaggcggg      60 gttttttcttg ttgacaagaa tcctcacaat accacagagt ctagactcgt ggtggacttc    120
tctcaatttt ctaggggag cacccacgtg                                       150

<210> SEQ ID NO 39
<211> LENGTH: 150
<212> TYPE: DNA
<213> ORGANISM: Hepatitis B virus

<400> SEQUENCE: 39
accgaacatg gagaacatca catcaggatt cctaggaccc ctgctcgtgt tacaggcggg      60 gttttttcttg ttgacaagaa tcctcacaat accgcagagt ctagactcgt ggtggacttc    120
tctcaatttt ctaggggag cacccgtgtg                                       150

<210> SEQ ID NO 40
<211> LENGTH: 150
<212> TYPE: DNA
<213> ORGANISM: Hepatitis B virus

<400> SEQUENCE: 40
gacgaacatg gagaacatca catcaggatt cctaggaccc ctgctcgtgt tacaggcggg      60 gttttttcttg ttgacaagaa tcctcacaat accgcagagt ctagactcgt ggtggacttc    120
tctcaatttt ctaggggat ctcccgtgtg                                       150
```

```
<210> SEQ ID NO 41
<211> LENGTH: 150
<212> TYPE: DNA
<213> ORGANISM: Hepatitis B virus

<400> SEQUENCE: 41
gacgaacatg gagaacatca catcaggatt cctaggaccc ctgctcgtgt tacaggcggg        60
gtttttcttg ttgacaagaa tcctcacaat accgcagagt ctagactcgt ggtggacttc       120
tctcagtttt ctaggggat  acccgtgtg                                         150

<210> SEQ ID NO 42
<211> LENGTH: 150
<212> TYPE: DNA
<213> ORGANISM: Hepatitis B virus

<400> SEQUENCE: 42
gctgaacatg gagaacatca catcaggatt cctaggaccc ctgctcgtgt tacaggcggg        60
gtttttcttg ttgacaagaa tcctcacaat accgcagagt ctagactcgt ggtggacttc       120
tctcaatttt ctaggggaa  ctaccgtgtg                                        150

<210> SEQ ID NO 43
<211> LENGTH: 150
<212> TYPE: DNA
<213> ORGANISM: Hepatitis B virus

<400> SEQUENCE: 43
gacgaacatg gagaacatca catcaggatt cctaggaccc ctgctcgtgt tacaggcggg        60
gtttttcttg ttgacaagaa tcctcacaat accgcagagt ctagactcgt ggtggacttc       120
tctcaatttt ctaggggat  acccgtgtg                                         150

<210> SEQ ID NO 44
<211> LENGTH: 150
<212> TYPE: DNA
<213> ORGANISM: Hepatitis B virus

<400> SEQUENCE: 44
tatgaacatg gacaacatca catcaggact cctaggaccc ctgctcgtgt tacaggcggt        60
gtgtttcttg ttgacaaaaa tcctcacaat accacagagt ctagactcgt ggtggacttc       120
tctcaatttt ctaggggaa  caccagggtg                                        150

<210> SEQ ID NO 45
<211> LENGTH: 150
<212> TYPE: DNA
<213> ORGANISM: Hepatitis B virus

<400> SEQUENCE: 45
tatgaacatg gacaacatca catcaggact cctaggaccc ctgctcgtgt tacaggcggt        60
gtgtttcttg ttgacaaaaa tcctcacaat accacagagt ctagactcgt ggtggacttc       120
tctcaatttt ctaggggaa  caccagggtg                                        150

<210> SEQ ID NO 46
<211> LENGTH: 150
<212> TYPE: DNA
<213> ORGANISM: Hepatitis B virus

<400> SEQUENCE: 46
tatgaacatg gagaacatca catcaggact cctaggaccc cttctcgtgt tacaggcggt        60
```

```
gtgtttcttg ttgacaaaaa tcctcacaat accacagagt ctagactcgt ggtggacttc    120
tctcaatttt ctaggggtac cacccgggtg                                      150

<210> SEQ ID NO 47
<211> LENGTH: 150
<212> TYPE: DNA
<213> ORGANISM: Hepatitis B virus

<400> SEQUENCE: 47
atcgaacatg gagagcacaa catcaggatt cctaggaccc ctgctcgtgt tacaggcggg    60
gtttttcttg ttgacaagaa tcctcacaat acctcagagt ctagactcgt ggtggacttc    120
tctcaatttt ctaggggag ctcccgcgtg                                       150

<210> SEQ ID NO 48
<211> LENGTH: 150
<212> TYPE: DNA
<213> ORGANISM: Hepatitis B virus

<400> SEQUENCE: 48
gctgaacatg gagaacatca catcaggatt cctaggaccc cttctcgtgt tacaggcggg    60
gtttttcttg ttgacaagaa tcctcacaat accgcagagt ctagactcgt ggtggacttc    120
tctcaatttt ctaggggaa ctaccgtgtg                                       150

<210> SEQ ID NO 49
<211> LENGTH: 150
<212> TYPE: DNA
<213> ORGANISM: Hepatitis B virus

<400> SEQUENCE: 49
gctgaacatg gagaacatca catcaggatt cctaggaccc ctgctcgtgt tacaggcggg    60
gtttttcttg ttgacaagaa tcctcacaat accgcagagt ctagactcgt ggtggacttc    120
tctcaatttt ctaggggaa ccaccgtgtg                                       150

<210> SEQ ID NO 50
<211> LENGTH: 150
<212> TYPE: DNA
<213> ORGANISM: Hepatitis B virus

<400> SEQUENCE: 50
actgaacatg gagaacatca catcaggatt cctaggaccc ctgctcgtgt tacaggcggg    60
gtttttcttg ttgacaagaa tcctcacaat accgcagagt ctagactcgt ggtggacttc    120
tctcaatttt ctaggggaa ctaccgtgtg                                       150

<210> SEQ ID NO 51
<211> LENGTH: 150
<212> TYPE: DNA
<213> ORGANISM: Hepatitis B virus

<400> SEQUENCE: 51
accgaacatg gagaacatcg catcaggact cctaggaccc ctgctcgtgt tacaggcggg    60
gtttttcttg ttgacaaaaa tcctcacaat accacagagt ctagactcgt ggtggacttc    120
tctcaatttt ctaggggaa cacccgtgtg                                       150

<210> SEQ ID NO 52
<211> LENGTH: 150
<212> TYPE: DNA
<213> ORGANISM: Hepatitis B virus
```

-continued

```
<400> SEQUENCE: 52
gttgaacatg gagaacatca catcaggatt cctaagaccc ctactcgtgt tacaggcggg      60
gtttttcttg ttgacaagaa tcctcacaat accgcagaat ctagactcgt ggtggacttc     120
tctcaatttt ctaggggget cacccgtgtg                                      150
```

What is claimed is:

1. A primer for PCR amplification capable of commonly amplifying different nucleic acid templates having mutated or polymorphic sites in their nucleotide sequences, said primer comprising abasic part in the region corresponding to the mutated or polymorphic sites of said different nucleic acid templates to be hybridized, wherein said primer commonly amplifies different nucleic acid templates having mutated or polymorphic sites in their nucleotide sequences at the same time.

2. The primer according to claim 1, wherein the abasic part is selected from the group consisting of dSpacer (5'-O-dimethoxytrityl-1',2'-dideoxyribose-3'-[(2-cyanoethyl)-(N,N-diisopropyl)]-phosphoramidite), 1'-OMe-dSpacer (5-O-dimethoxytrityl-1'-methoxy-2'-dideoxyribose-3'-[(2-cyanoethyl)-(N,N-diisopropyl)]-phosphoramidite), PC Spacer Phosphoamidite ([4-(4,4'-Dimethoxytrityloxy)butyramidomethyl)-1-(2-nitrophenyl)-ethyl]-2-cyanoethyl-(N,N-diisopropyl)-phosphoramidite), rSpacer CE Phosphoamidite (5'-O-Dimethoxytrityl -1'-Deoxyribose-2'-O-Triisopropylsilyloxymethyl-3'-[(2-cyanoethyl)-(N,N-diisopropyl)]-phosphoramidite), Spacer C12 CE Phosphoamidite (12-(4,4'-Dimethoxytrityloxy)-dodecyl-1-[(2-cyanoethyl)-(N,N-diisopropyl)]-phosphoramidite), Spacer Phosphoamidite 18 (18-O-Dimethoxytritylhexaethyleneglycol,1-[(2-cyanoethyl)-(N,N-diisopropyl)]-phosphoramidite), Spacer Phosphoamidite 9 (9-0-Dimethoxytrityl-triethyleneglycol, 1-[(2-cyanoethyl)-(N,N-diisopropyl)]-phosphoramidite), and Spacer Phosphoamidite C3 (3-(4,4'-Dimethoxytrityloxy)propyl-1-[(2-cyanoethyl)-(N,N-diisopropyl)]-phosphoramidite).

3. The primer according to claim 1, wherein the number of the abasic part in the primer is 1-10.

4. The primer according to claim 3, wherein the number of the abasic part in the primer is 1-3.

5. The primer according to claim 1, wherein a nucleotide complementary to template is added to a terminus of the primer to compensate the lowered Tm by abasic part.

6. A composition for PCR amplification comprising reaction buffer, 4 kinds of dNTPs, DNA polymerase and any primer for PCR amplification according to claim 1.

7. The composition according to claim 6, wherein the composition further comprises a dye and/or a stabilizer.

8. The composition according to claim 7, wherein the dye is one or more compounds selected from the group consisting of Bromophenol blue, Xylene cyanole, Bromocresol red and Cresol red.

9. The composition according to claim 7, wherein the stabilizer is one or more compounds selected from the group consisting of gelatin, bovine serum albumin, Thesit, PEG-8000 and polyol.

10. A method for PCR amplification comprising the steps of mixing the composition for PCR amplification comprising the primer according to claim 1 with nucleic acid template; and performing PCR with the mixture.

11. The method for PCR amplification according to claim 10, wherein the method is to commonly amplify different nucleic acid templates having mutated sites in their nucleotide sequences.

12. The method for PCR amplification according to claim 10, wherein the method is to commonly amplify different nucleic acid templates having polymorphic sites in their nucleotide sequences.

13. The method for PCR amplification according to claim 10, wherein one primer of the primer set for PCR amplification is a primer for PCR amplification comprising abasic part and the other primer of the primer set is a normal primer not comprising abasic parts.

14. The primer of claim 2, wherein a nucleotide complementary to template is added to a terminus of the primer to compensate the lowered Tm by abasic part.

15. The primer of claim 3, wherein a nucleotide complementary to template is added to a terminus of the primer to compensate the lowered Tm by abasic part.

16. The primer of claim 4, wherein a nucleotide complementary to template is added to a terminus of the primer to compensate the lowered Tm by abasic part.

* * * * *